(12) United States Patent
Gyure et al.

(10) Patent No.: US 6,663,603 B1
(45) Date of Patent: *Dec. 16, 2003

(54) LOCALIZED LUBRICATION OF SYRINGE BARRELS AND STOPPERS

(75) Inventors: Sandor Gyure, West Orange, NJ (US); Terry L. Sprieck, Columbus, NE (US); Duane L. Schmitt, Columbus, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/494,583

(22) Filed: Jan. 31, 2000

Related U.S. Application Data

(63) Continuation of application No. 09/092,757, filed on Jun. 5, 1998.

(51) Int. Cl.[7] ............................................. A61M 5/315
(52) U.S. Cl. ........................ 604/230; 604/230; 427/2.3
(58) Field of Search .................................. 604/230, 231, 604/265, 228; 728/898; 427/2.12, 2.18, 2.25, 2.28, 2.3; 401/4

(56) References Cited

U.S. PATENT DOCUMENTS

| | | | |
|---|---|---|---|
| 4,997,423 A | | 3/1991 | Okuda et al. |
| 5,213,839 A | | 5/1993 | Awazu et al. |
| 5,456,940 A | * | 10/1995 | Funderburk .................. 604/265 |
| 5,662,960 A | | 9/1997 | Hostettler et al. |
| 5,713,857 A | * | 2/1998 | Grimard et al. ............ 604/218 |

* cited by examiner

Primary Examiner—Manuel Mendez
(74) Attorney, Agent, or Firm—Hoffmann & Baron, LLP

(57) ABSTRACT

A medical syringe assembly includes a first opening and a second opening at opposite ends of a tubular barrel having an inner wall. The inner wall includes an inner surface. A stopper having an engagement surface is slidably received in the tubular barrel and includes a portion for engaging the surface of the inner wall of said tubular barrel. A lubricant is disposed over a limited area of at least one member of the inner wall of the tubular barrel and the engagement surface of said stopper, whereby a sufficient amount of the lubricant is available to provide adequate reduction of friction between the surface of the inner wall of the tubular barrel and the engagement surface of the stopper.

12 Claims, 1 Drawing Sheet

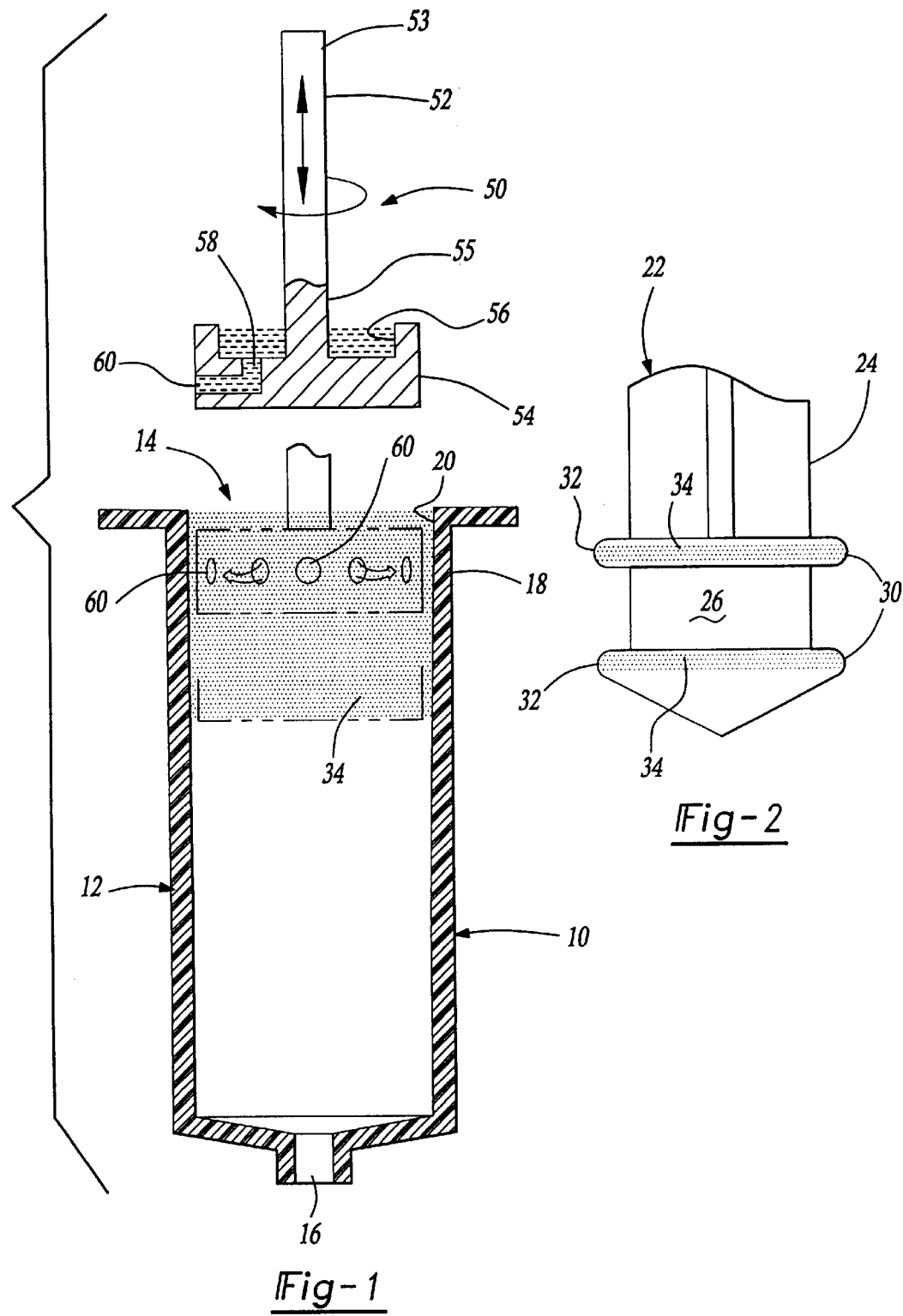

LOCALIZED LUBRICATION OF SYRINGE BARRELS AND STOPPERS

This application is a continuation of patent application Ser. No. 09/092,757 filed on Jun. 5, 1998. The subject invention relates to medical syringes and, more specifically, to the lubrication of syringe barrels and stoppers.

TECHNICAL FIELD

BACKGROUND OF THE INVENTION

By way of background, syringes typically include a tubular barrel portion and a plunger having a stopper disposed at one end. The plunger and stopper are inserted into the tubular barrel of the syringe. The stopper portion is typically made of an elastomeric material, such as natural or synthetic rubber, which engages an inner surface of the syringe tubular barrel to create a seal that facilitates ejecting a fluid from the syringe when pressure is applied to the plunger.

Traditionally, the inside of the syringe tubular barrels, whether constructed of plastic or glass, and the outside of the stoppers have been lubricated with a silicone oil to reduce the friction between the two parts. By selecting the viscosity and the amount of silicone applied to the inside of the tubular barrel and to the stopper, the friction between them is reduced or adjusted to a desired level.

In conventional syringe fabrication, silicone is applied to the syringe tubular barrels by spraying the silicone oil downwardly into the tubular barrel. This generally results in the entire inside surface of the tubular barrel being covered with silicone. Likewise, the entire stopper typically is coated with silicone oil in a batch process in which a number of stoppers are tumbled together with silicone oil. In both of these processes, the entire inside surface of the syringe barrel and the entire stopper is covered with silicone. In this case, the resultant amount of silicone applied to the syringe barrel and the stopper exceeds what is required to sufficiently reduce the friction between the two parts to a suitable level.

While medical grade silicone oils are not typically harmful, it is desirable to have a medical syringe and method for making the medical syringe that minimizes the amount of silicone used and more effectively and strategically places silicone on the syringe components to reduce the friction between the moving parts of the syringe while eliminating excess lubricant. The advantages of minimizing the amount of silicone which is injected into the body of a patient or subject along with the drug, preventing the leakage of silicone to the outside of the syringe thereby reducing the likelihood that the syringe will slip in the hands of a medical practitioner, and minimizing the interaction between the lubricant (silicone) and the contents of the syringe. Minimizing the interaction between the lubricant and the contents of the syringe is particularly important where syringes are pre-loaded with a particular injectable drug, which may be stored for some time before being administered to a patient.

Accordingly, it is desirable and advantageous to have a medical syringe assembly and method for making a medical syringe assembly in which lubricant is only disposed over a limited area of the syringe in a sufficient amount to provide adequate reduction of friction between the syringe barrel and the stopper.

SUMMARY OF THE INVENTION

A medical syringe assembly for administering an injectable drug includes a tubular barrel having an inner wall. A plunger includes a stopper having an engagement surface in slidable engagement with the surface of the inner wall of the tubular barrel. A lubricant is disposed over a limited area of at least one portion of the inner wall of the tubular barrel and the engagement surface of the stopper whereby a sufficient amount of the lubricant is available to adequately reduce friction between the surface of the inner wall of the tubular barrel and the engagement surface of the stopper.

The method of this invention is useful for applying a lubricant on a surface of the inner wall of a tubular barrel of a medical syringe assembly over an area extending completely circumferentially around the tubular barrel and extending axially from a first opening of the tubular barrel along a distance less than the entire length of the inner wall of the tubular barrel. The method includes providing an applicator including a container for holding the lubricant. The container preferably has a sidewall with at least one aperture. One end of the applicator is disposed into the first opening of the tubular barrel and the applicator is rotated while depositing the lubricant against the inner wall of the tubular barrel. The applicator moves axially into the tubular barrel as the applicator is rotating for a distance less than the axial length of the inner wall of the tubular barrel. The applicator is removed when the desired amount of the tubular barrel has been coated with the lubricant.

A method for coating a stopper of a medical syringe assembly with a lubricant over a circumferential area less than the total circumferential area of the stopper is also disclosed which includes providing the stopper with annular ribs, each rib including an outer surface, and pattern coating the outer surface of each rib with a lubricant. The conical area at the leading end of the stopper also should not have lubricant.

Also there is disclosed a method for coating a stopper of a medical syringe assembly with a lubricant over a circumferential area less that the total circumferential area of the stopper which includes pattern coating the outer surface of the stopper having one or more annular rings with lubricant wherein the combined axial length of the annular rings is less than the axial length of the outer surface of the stopper.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a cross-sectional view of a syringe barrel and coating apparatus of the subject invention; and FIG. 2 is a side view of a portion of a plunger including a stopper of the subject invention.

DETAILED DESCRIPTION OF THE PREFERRED EMBODIMENT

Referring to the Figures, wherein like numerals indicate like and corresponding parts throughout the several views, a medical syringe assembly is shown generally at 10. The syringe assembly 10 is of the type to be utilized for the administration and injection of injectable drugs.

The syringe assembly 10 includes a generally cylindrical or tubular barrel 12 having a mouth opening 14 disposed at one end and an outlet 16 disposed at the opposite end. A continuous circumferential wall 18 defines the tubular barrel 12. A lubricant 34 is disposed on a portion of an inner surface 20 of the wall 18. The lubricant 34 is preferably only disposed over a limited area of the inner surface 20 of the tubular barrel 12.

Referring specifically to FIG. 2, a plunger 22 includes a shaft portion 24 having a stopper 26 disposed at its distal end. The stopper 26 is preferably constructed of an elastomeric material such as a synthetic rubber which conforms to the dimensions of the barrel 12, defined by the wall 18, to provide a seal therebetween. The stopper 26 includes a conical portion 28 disposed at the most distal end of the stopper 26. The stopper 26 also includes at least one annular rib 30 that includes an engagement surface 32 for engaging the inner surface 20 of the wall 18 of the tubular barrel 12. The engagement surface 32 of each rib 30 preferably is coated with the lubricant 34 to aid in the reduction of friction between the stopper and the inner surface 20 of the tubular barrel 12.

The tubular barrel 12 and plunger shaft 24 can be constructed of any suitable material. For example, the tubular barrel 12 and the plunger shaft 24 can each be constructed of a suitable material such as glass or plastic. Plastics are the preferred materials as they are more easily manufactured and can be easily disposed.

The inner surface 20 of the tubular barrel 12 extends completely circumferentially around the inner wall 18 and extends axially from the mouth 14 of the tubular barrel 12 to the outlet 16.

Referring specifically to FIG. 1, a coating head assembly 50 for applying the lubricant 34 to the inner surface 20 of the tubular barrel 12 is shown schematically. The coating head assembly 50 includes a spindle 52 which includes a proximal end 53 and a distal end 55. The proximal end 53 can be attached to a mechanism (not shown) for rotating the spindle 52 and moving it axially (i.e., up and down according to the drawing). A coating head 54 is attached to the distal end 55 of the spindle 52. The coating head 54 includes a lubricant reservoir 56 for supplying lubricant 34 for coating the inner surface 20 of the tubular barrel 12. A passageway 58 is disposed in communication with the reservoir 56 and at least one aperture 60 disposed in the coating head 54 for permitting the lubricant 34 to exit the reservoir and be applied to the inner surface 20 of the tubular barrel 12.

In operation, the coating head assembly 50 is placed into the mouth 14 of the tubular barrel 12 and is then axially displaced downwardly from the mouth 14 of the tubular barrel 12. The assembly 50 only moves a distance sufficient to coat a preselected portion of the inner surface 20 of the wall 18. Following the coating of the selected portion of the inner surface 20 of the tubular barrel 12, the coating head 54 is withdrawn from the tubular barrel 12.

The amount of lubricant 34 applied to the inner surface 20 of the tubular barrel 20 can be adjusted by selecting a predetermined pattern for the apertures 60 disposed in the rotating coating head 54, by varying the size of the apertures 60, the speed of rotation of the coating head 54, the depth of travel of the coating head 54, and controlling the amount of lubricant which is initially deposited into reservoir 56 and the amount which is radially dispensed against the inner surface 20 of the tubular barrel 12.

The application of the lubricant 34 preferably extends completely circumferentially around the inner surface 20 but extends axially only from near the mouth 14 of the tubular barrel 12 along a distance less than the entire length of the wall 18 of the tubular barrel 12. That is, the lubricant 34 preferably is disposed only on the inner surface 20 of the tubular barrel 12 at an area extending completely circumferentially around the tubular barrel 12 but extending axially only from near the mouth 14 of the tubular barrel 12 along a distance which is only a portion of the length of the wall 18 of the tubular barrel 12. In the preferred embodiment, the lubricant 34 extends axially from near the mouth 14 of the tubular barrel 12 along a distance that is only slightly greater than the length of the stopper 26 of the plunger 22. Since the stopper 26 will typically be maintained near the mouth 14 in a prefilled syringe assembly, the lubricant 34 need only coat the corresponding area of the inner wall 20 to achieve the desired lubrication.

Also in order to minimize the amount of lubricant 34 utilized in the syringe assembly 10, the lubricant preferably is disposed on the outer surface 27 of the stopper 26 in an annular pattern having an axial length smaller than the axial length of the stopper 26. That is, the lubricant 34 preferably is disposed only on discrete annular portions of the stopper 26. Preferably, as described above, the stopper 26 includes at least one annular rib 30 with the lubricant 34 disposed only on the outer or engagement surface 32 of each of the annular ribs 30. Since the engagement surface 32 of each rib 30 is the only portion of the stopper 26 in contact with the inner surface 20 of the wall 18 of the tubular barrel 12, by applying the lubricant 34 to only the engagement surface 32 of each rib 30, the total amount of lubricant utilized can be greatly reduced while reducing friction between the stopper 26 and the tubular barrel 12.

The application of the lubricant to the selected areas of the stopper 26 can be accomplished by adapting known methodologies from the printing arts such as pattern coating or by transferring a thin layer of lubricant to selected areas of the stopper 26 by rolling and pressing. Additionally, lubricant 34 can be applied to the selected areas of the stopper 26 by masking or covering those portions of the stopper 26 to which no lubricant 34 is to be applied, while applying, preferably by spraying, the lubricant 34 onto the remaining, unmasked portions of the stopper 26.

The lubricant 34 is preferably a medical grade silicone oil. Other suitable medical lubricants, such as glycerin, may be utilized without departing from the spirit of the invention.

The invention has been described in an illustrative manner, and it is to be understood that the terminology which has been used is intended to be in the nature of words of description rather than of limitation.

Modifications and variations of the present invention are possible in light of the above teachings. It is, therefore, to be understood that within the scope of the following claims, the invention may be practiced otherwise than as specifically described above.

What is claimed is:

1. A medical syringe assembly comprising:
    a tubular barrel having a first opening and a second opening at opposite ends with a wall extending between said ends, said wall having an inner surface;
    a stopper slidably received in said tubular barrel and having a portion in slidable engagement with said inner surface of said tubular barrel; and
    a lubricant disposed over a limited area of at least one portion of said inner surface of said tubular barrel whereby a sufficient amount of said lubricant is available to reduce friction between said inner surface and said stopper.

2. A medical syringe assembly according to claim 1, wherein said lubricant is provided on said inner surface portion extending completely circumferentially around said inner wall but extending axially only from near said first opening along a distance that is less than an entire length of said inner surface.

3. A medical syringe assembly according to claim 2, wherein said lubricant extends from near said first opening of said tubular barrel along a distance which is approximately equal to an axial length of said stopper.

4. A medical syringe assembly according to claim 1, wherein said stopper has an outer engagement surface and said lubricant is provided on a portion of said outer surface that is less than an axial length of said stopper.

5. A medical syringe assembly according to claim 1, wherein said stopper includes an annular rib having an outer surface, and said lubricant is provided only on said outer surface of said annular rib.

6. A medical syringe assembly according to claim 1, wherein said lubricant is provided on said inner surface over an area extending completely circumferentially around said inner surface but extending axially from near said first opening along only a minor portion of a length of said tubular barrel, and wherein said lubricant is additionally provided on an engagement surface of said stopper in an annular pattern having an axial length smaller than an axial length of said stopper.

7. A medical syringe assembly according to claim 1, wherein said syringe is formed of glass.

8. A medical syringe assembly according to claim 1, wherein said syringe is formed of a plastic material.

9. A medical syringe assembly according to claim 1, wherein said lubricant comprises silicone.

10. A method of lubricating a syringe assembly including a stopper that is received with a syringe barrel, comprising the steps of:
   (a) selecting a portion of the stopper that has an axial length that is less than a total axial length of the stopper; and
   (b) applying a lubricant only to the portion from step (a).

11. The method of claim 10, wherein step (b) includes masking another portion of the stopper and applying the lubricant to the unmasked portion of step (a).

12. The method of claim 10, wherein the portion of step (a) comprises an annular rib and step (b) includes pressing the lubricant onto the rib.

* * * * *